United States Patent
Ferraro et al.

(10) Patent No.: US 9,561,355 B2
(45) Date of Patent: Feb. 7, 2017

(54) METHOD FOR MAKING AN ARRAY OF MICRO-NEEDLES

(71) Applicants: CONSIGLIO NAZIONALE DELLE RICERCHE, Rome (IT); FONDAZIONE ISTITUTO ITALIANO DI TECNOLOGIA, Genoa (IT)

(72) Inventors: Pietro Ferraro, Naples (IT); Sara Coppola, Sorrento (IT); Andrea Finizio, Bacoli (IT); Simonetta Grilli, Naples (IT); Veronica Vespini, Caserta (IT); Paolo Antonio Netti, Naples (IT); Raffaele Vecchione, Arzano (IT); Eliana Esposito, Marigliano (IT)

(73) Assignees: CONSIGLIO NAZIONALE DELLE RICERCHE, Rome (IT); FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 12 days.

(21) Appl. No.: 14/767,073

(22) PCT Filed: Feb. 11, 2014

(86) PCT No.: PCT/IT2014/000036
§ 371 (c)(1),
(2) Date: Aug. 11, 2015

(87) PCT Pub. No.: WO2014/125515
PCT Pub. Date: Aug. 21, 2014

(65) Prior Publication Data
US 2015/0374966 A1   Dec. 31, 2015

(30) Foreign Application Priority Data

Feb. 12, 2013   (IT) .............................. RM2013A0079

(51) Int. Cl.
*A61M 5/00*   (2006.01)
*A61M 37/00*   (2006.01)
(Continued)

(52) U.S. Cl.
CPC ...... *A61M 37/0015* (2013.01); *B29C 37/0053* (2013.01); *B29C 59/025* (2013.01);
(Continued)

(58) Field of Classification Search
CPC .................. A61M 2037/0053; B81C 1/00214; B81C 1/00015; B81C 1/00111; B29C 67/007
(Continued)

(56) References Cited

U.S. PATENT DOCUMENTS

2005/0258573 A1   11/2005   Minegishi et al.
2011/0240201 A1   10/2011   Jung et al.

FOREIGN PATENT DOCUMENTS

WO   2009072830 A2   6/2009

OTHER PUBLICATIONS

International Search Report for PCT/IT2014/000036 mailed on May 22, 2014.

*Primary Examiner* — Deanna K Hall
(74) *Attorney, Agent, or Firm* — Thomas Horstemeyer, LLP

(57) ABSTRACT

There is described a method for making an array of micro-needles, comprising the steps of:
  depositing a plurality of drops of a liquid substance comprising a polymer on a surface of a starting substrate;
  positioning a pyroelectric substrate at a certain distance from the starting substrate in such a way that the drops deposited are positioned between said surface of the starting substrate and a surface of the pyroelectric substrate;

(Continued)

varying the temperature of the pyroelectric substrate or a part thereof to induce on said surface of the pyroelectric substrate a charge density such that starting from the drops deposited, under the effect of an electrodynamic force, respective cones are formed having a tip facing towards the pyroelectric substrate;

determining a consolidation of the cones, to form said micro-needles, preventing the tip of said cones from contacting said surfaces of the pyroelectric substrate.

18 Claims, 2 Drawing Sheets

(51) Int. Cl.
*B29C 37/00* (2006.01)
*B29C 59/02* (2006.01)
*B81C 1/00* (2006.01)
B29L 31/00 (2006.01)

(52) U.S. Cl.
CPC .. *B81C 1/00111* (2013.01); *A61M 2037/0046* (2013.01); *A61M 2037/0053* (2013.01); *B29L 2031/7544* (2013.01); *B81B 2201/055* (2013.01)

(58) Field of Classification Search
USPC .......................................................... 604/173
See application file for complete search history.

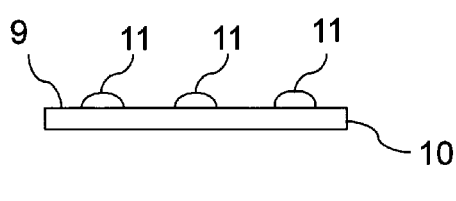
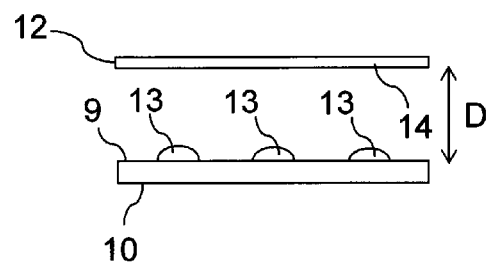
FIG. 2        FIG. 3
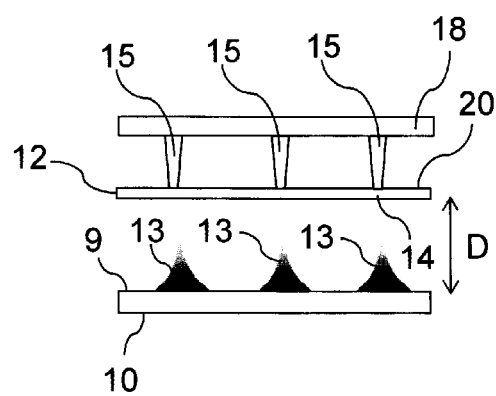
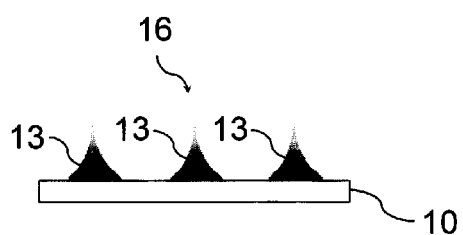
FIG. 4        FIG. 5

METHOD FOR MAKING AN ARRAY OF MICRO-NEEDLES

CROSS-REFERENCE TO RELATED APPLICATION

This application is the 35 U.S.C. §371 national stage application of PCT Application No. PCT/IT2014/000036, filed Feb. 11, 2014, which claims priority to and the benefit of, IT Patent Application No. RM2013A000079, filed Feb. 12, 2013, both of which are herein incorporated by reference in their entirety.

The present description relates to the technical field of devices for the epidermal administration of pharmaceutical products or active ingredients and/or devices for the transdermal sampling of biological fluids and in particular it relates to a method for making an array of micro-needles.

It is known to use arrays of micro-needles for the transdermal administration of pharmaceutical products or active ingredients. Such a technique is advantageous as it allows replacing the use of hypodermic syringes with millimetric needles which, puncturing the skin, cause pain and may give rise to other problems, such as causing an infection.

It is also known to make the above-mentioned arrays of micro-needles using biodegradable materials, so that said micro-needles, if used in drug or active ingredient delivery devices, will dissolve over time in the epidermis after their penetration without leaving traces in the epidermis itself.

Methods are known for making the arrays of micro-needles which are based on moulding, which typically comprise the following steps: making a master structure, making a three-dimensional mould with an array of recesses, filling the mould with a mixture comprising a polymer and a drug or an active ingredient, hardening the polymer, separating the array of micro-needles from the three-dimensional mould.

Due to the contact with the mould, the production methods described above generally have several drawbacks, such as a large number of steps and process conditions causing damage to the encapsulated drug and a possible break-up of micro-needles and also require appropriate precautions to preserve the hygiene of the mould so that it does not contaminate the micro-needles.

A general object of the present description is to provide a process for making an array of micro-needles which does not have the drawbacks mentioned above with reference to the prior art.

This and other objects are achieved by a method for making an array of micro-needles as defined in claim 1 in the most general form thereof and in the dependent claims in some particular embodiments thereof.

The invention will be better understood from the following detailed description of embodiments thereof, made by way of an example and therefore in no way limiting with reference to the accompanying drawings, in which:

FIG. 2 shows a side view of a starting substrate on which an array of drops has been deposited;

FIG. 3 shows a side view of the starting substrate in FIG. 1 and a pyroelectric substrate;

FIG. 4 shows a side view of the starting substrate and a pyroelectric substrate during one of the steps of the method in FIG. 1;

FIG. 5 shows a side view of an array of micro-needles obtained by the production method in FIG. 1.

In the accompanying figures, elements which are equivalent or similar will be indicated by the same reference numerals.

Figure 1:
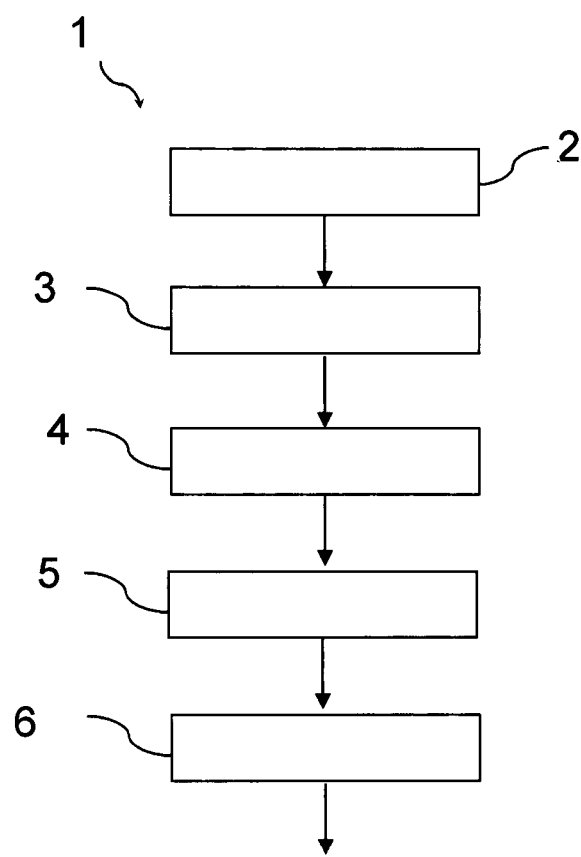
FIG. 1 shows a schematic flow diagram of an embodiment of a method for making an array of micro-needles.

FIG. 1 shows a schematic flow diagram of an embodiment of a method 1 for making an array 16 of micro-needles 13.

Method 1 comprises a step of depositing 3 a plurality of drops 11 of a liquid substance comprising a polymer on a surface 9 of a starting substrate 10, or base substrate 10.

According to an embodiment, the above polymer is PLGA—poly lactic glycolic acid. According to alternative embodiments, the above polymer is a biocompatible polymer of a type other than the PLGA, such as PVP (polyvinylpyrrolidone), or maltose, or PPF (Poly propylene fumarate), or CMC (carboxy methyl cellulose), or PHEMA (Poly hydroxyethyl-methacrylate), or cellulose, or dextrin or an ester-based biopolymer containing micro particles of hydrogel to improve the timing of release and allow a greater number of drugs or active substances of a hydrophilic nature as compared to the lipophilic one of esters. The above polymers, in addition to being biocompatible, have the advantage of having an adequate mechanical strength required for the transdermal penetration.

According to an embodiment, the above-mentioned liquid substance comprises a drug and/or an active ingredient. In this case, array 16 of micro-needles 13 may be part of a device for the transdermal delivery of said drug and/or said active ingredient. For example, the above device is a bracelet.

For example, the above drug and/or active ingredient is a vaccine, but clearly there are no limitations to the type of drug and/or active ingredient that can be used in the above substance compared to drugs and/or active ingredients that a man skilled in the art knows that may be incorporated in a polymeric micro-needle and administered transdermally.

According to an embodiment, said substance comprises a solvent provided to keep said polymer in the liquid state so that the deposition in drops of said substance on the starting substrate is possible.

According to an embodiment, the solvent may be DCM—dichloromethane—or DMC—dymethylcarbodimmide. According to an advantageous embodiment from the point of view of the quality of the final result of the process for making array 16 of micro-needles 13, the concentration of the solvent in said solution is in the range 20%-30% and preferably is equal to 25% or to about 25%.

According to an embodiment, the above solution has a viscosity in the range [10-1000] $mm^2/s$ inclusive and preferably in the range [100-200] $mm^2/s$ inclusive.

As regards the starting substrate 10, or base substrate 10, according to an embodiment, said substrate is flexible in order to adequately adhere to the epidermis. According to an embodiment, said substrate is a flexible plate-shaped substrate made of PDMS—poly-dimethyl-siloxane.

The array of drops 11 deposited on the starting substrate 10 may have different shapes, an array of drops having a linear, circular, rectangular shape, etc., being for example deposited.

With reference to FIG. 1, the depositing step 3 may be preceded by a step of preparation of the substance, which for example comprises a step of mixing the solvent, the biodegradable polymer and the drug and/or active ingredient.

With reference to FIGS. 1 and 3, the production method includes a step of positioning 4 a pyroelectric substrate 12 at a certain distance D from the starting substrate 10 so that drops 11 deposited on surface 9 of the starting substrate 10 are interposed between said surface 9 and a surface 14 of the pyroelectric substrate 12.

According to a possible embodiment, the pyroelectric substrate 12 is a crystal of lithium niobate (LN) or lithium tantalate (LT), for example a crystal of periodically polarized lithium niobate (PPLN).

With reference to FIGS. 1 and 4, the production method 1 comprises a step of varying the temperature 5 of the pyroelectric substrate 12 or a part thereof to induce on surface 14 of the pyroelectric substrate 12 a charge density such that starting from the drops deposited 11, under the effect of an electrodynamic force, respective cones 13 are formed having a tip facing towards the pyroelectric substrate 12.

For example, the above-mentioned step of varying the temperature 5, comprises an operation of heating portions of the pyroelectric substrate 12 in positions corresponding to the drops deposited 11. This may for example be obtained by means of a heating device 18 comprising an array of tips 15 configured to contact surface 20 of the pyroelectric substrate 12 opposite to surface 14. In an alternative embodiment, the above heating device is such as to emit a collimated optical radiation beam, such as produced by laser sources, to heat substrate 12 in positions corresponding to the drops deposited 11.

The production method 1 further comprises a step of determining 6 a progressive consolidation of cones 13 preventing the tip thereof 13 from contacting surface 14 of the pyroelectric substrate 12. According to one embodiment, this can be achieved if distance D is greater than the critical distance Dc given by:

$$Dc=(1+\theta/4)V^{1/3}$$

in which θ and V respectively represent the angle of contact and the volume of drops 11.

According to an embodiment, it is possible to provide an operation in the production method 1 to distance the two substrates 10, 12 from each other before or during the above step 6 of determining the consolidation. According to an advantageous embodiment, the above distancing operation takes place after the formation of cones 13 and before the final consolidation thereof and during the above operation of distancing the two substrates 10, 12, these can be made to translate with respect to each other to increase distance D.

In an alternative embodiment, the above distancing operation is carried out by distancing the two substrates 10, 12 from each other substantially so as to completely annul the electrodynamic effects of the pyroelectric substrate 12 on cones 13.

If the liquid substance of drops 11 contains a solvent, during the forming step and during the gradual consolidation of cones 13, an evaporation of the solvent and a progressive solidification of cones 13 take place.

According to a more general embodiment, an initial step of the formation of cones 13 takes place in an atmosphere at a first temperature and step 6 of determining the consolidation takes place in an atmosphere at second temperature higher than the first temperature. According to a more particular embodiment, the first temperature is the ambient temperature while the second temperature is a temperature between 35° C. and ° C., and preferably equal to about 40° C. More preferably, during the step of determining the consolidation, cones 13 are kept in an atmosphere at the second temperature for about 10 minutes.

Moreover, an embodiment is advantageous wherein the steps of varying the temperature 5 and of determining the consolidation 6 are performed in such a way as to prevent said cones 13, all or most thereof, from deforming to the point of forming bridges between substrates 10, 12.

The height of the cones obtained, in other words of the micro-needles, is preferably in the range [200 and 800] micron inclusive, and preferably in the range [400-800] micron inclusive. By controlling the volume of drops it is possible to control the size of the cones obtained 13, thus of the micro-needles. In fact, an increase in the volume of the droplets results in an increase in the height of the cones, improving the aspect-ratio.

Experimental tests have shown that a production method 1 of the type described above allows the objects mentioned above with reference to the prior art to be achieved. Indentation tests in the epidermis were successfully carried out.

It is noted that the above method of production, thanks to the provision of preventing the cones from contacting the pyroelectric substrate, allows the micro-needles to be kept uncontaminated and not to expose said micro-needles at high temperatures, which could damage the drug, or the active substance encapsulated in the micro-needles. Moreover, the above method of production is particularly cost-effective.

The principle of the invention being understood, the manufacturing details and the embodiments may widely vary compared to what described and illustrated by way of a non-limiting example only, without departing from the scope of the invention as defined in the accompanying claims.

The invention claimed is:

1. Method for making an array of micro-needles, comprising the steps of:
   depositing a plurality of drops of a liquid substance comprising a polymer on a surface of a starting substrate;
   positioning a pyroelectric substrate at a certain distance from the starting substrate in such a way that the drops deposited are positioned between said surface of the starting substrate of the pyroelectric substrate;
   varying the temperature of the pyroelectric substrate or a part thereof to induce on said surface of the pyroelectric substrate a charge density such that starting from the drops deposited, under the effect of an electrodynamic force, respective cones are formed having a tip facing towards the pyroelectric substrate;
   determining a consolidation of the cones, to form said micro-needles, preventing the tip of said cones from contacting said surfaces of the pyroelectric substrate.

2. Method according to claim 1, wherein the liquid substance contains a solvent and wherein during said formation and said consolidation of the cones there is an evaporation of the solvent and a progressive solidification of the cones.

3. Method according to claim 2, wherein an initial step of said formation of the cones takes place in an atmosphere at a first temperature and wherein said step of determining the consolidation takes place in an atmosphere at second temperature higher than the first temperature.

4. Method according to claim 3, wherein the first temperature is ambient temperature and wherein the second temperature is a temperature of 35° C. to 45° C.

5. Method according to claim 2, wherein said polymer is a PLGA—poly-lactic glycolic acid, or a biocompatible polymer from those listed below: PVP (polyvinylpyrrolidone), or maltose, or PPF (Poly propylene fumarate), or CMC (carboxy methyl cellulose), or PHEMA (Poly hydroxyethyl-methacrylate), or cellulose or dextrin or an ester-based biopolymer containing micro particles of hydrogel.

6. Method according to claim 2, wherein said solvent is DCM—dichloromethane or DMC—dimethyl carbon dimmide.

7. Method according to claim 6, wherein the concentration of the solvent in said substance is comprised in the range 20% to 30%.

8. Method according to claim 6, wherein the concentration is equal to 25%.

9. Method according to claim 1, wherein said substance has a viscosity in the range of [10-1000] mm$^2$/s inclusive.

10. Method according to claim 9, wherein said viscosity is in the range of [100-200] mm$^2$/s inclusive.

11. Method according to claim 1, wherein the starting substrate is a flexible plate-shaped substrate made from PDMS—poly dimethyl siloxane.

12. Method according to claim 1, wherein said distance is a distance greater than the critical distance Dc given by:

$$Dc=(1+\theta/4)V^{1/3}$$

in which θ and V respectively represent the contact angle and the volume of said drops.

13. Method according to claim 1, wherein said steps of varying the temperature and of determining the consolidation are performed in such a way as to prevent said cones, all or most thereof, from deforming to the point of forming bridges between the substrates.

14. Method according to claim 1, further comprising an operation of distancing the substrates before or after said step of determining the consolidation.

15. Method according to claim 1, wherein said substance comprises a pharmaceutical product and/or an active ingredient.

16. Array of micro-needles characterized in that said array is obtained using a production method according to claim 1, and comprising said micro-needles and said substrate, wherein said micro-needles are attached to, and project from, said starting substrate.

17. Transdermal release or transdermal sampling device comprising an array of micro-needles according to claim 16.

18. Transdermal release or transdermal sampling device according to claim 17, wherein said device is a bracelet.

* * * * *